United States Patent [19]

Clark et al.

[11] Patent Number: 5,124,500
[45] Date of Patent: Jun. 23, 1992

[54] PROCESS FOR REMOVING HYDROGEN FROM THE PRESENCE OF ORGANIC COMPOUNDS

[75] Inventors: David M. Clark; Pierre E. Dejaifve; Christopher S. John; Jaydeep Biswas; Ian E. Maxwell, all of Amsterdam, Netherlands

[73] Assignee: Shell Oil Company, Houston, Tex.

[21] Appl. No.: 560,640

[22] Filed: Jul. 31, 1990

[30] Foreign Application Priority Data

Jan. 29, 1990 [GB] United Kingdom ............... 9001956

[51] Int. Cl.$^5$ ............................................. C07C 5/327
[52] U.S. Cl. .................................. 585/655; 423/248; 423/648.1; 55/75
[58] Field of Search ............... 585/655; 208/299, 305; 423/248, 648.1; 55/75, 16

[56] References Cited

U.S. PATENT DOCUMENTS 2,882,243  4/1959  Milton ..................................... 55/75
4,788,371  11/1988  Imai et al. ........................... 585/443

FOREIGN PATENT DOCUMENTS 0219271  4/1987  European Pat. Off. .
0219272  4/1987  European Pat. Off. .

Primary Examiner—Curtis R. Davis
Assistant Examiner—William L. Diemler

[57] ABSTRACT

A process for the removal of hydrogen from a mixture of hydrogen and one or more organic compounds, which comprises contacting the mixture with a molecular sieve containing a reducible metal cation, said molecular sieve being selectively permeable to hydrogen.

10 Claims, No Drawings

PROCESS FOR REMOVING HYDROGEN FROM THE PRESENCE OF ORGANIC COMPOUNDS

FIELD OF THE INVENTION

The present invention relates to a process for the removal of hydrogen from a mixture of hydrogen and one or more organic compounds. It also relates to a process for the dehydrogenation of organic compounds which involves the removal of hydrogen obtained by the dehydrogenation.

BACKGROUND OF THE INVENTION

It is often desirable to remove hydrogen from a mixture of hydrogen and one or more organic compounds, for example in a process for the dehydrogenation of organic compounds.

In a process for the dehydrogenation of organic compounds, the position of thermodynamic equilibrium between dehydrogenatable organic compounds and dehydrogenated organic compounds depends upon the amount of hydrogen present. This may be appreciated from the equation give below:

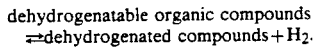

dehydrogenatable organic compounds
$\rightleftharpoons$ dehydrogenated compounds + $H_2$.

Accordingly, in a dehydrogenation process, it may be desirable to remove hydrogen from a mixture of hydrogen and dehydrogenatable and dehydrogenated organic compounds in order to shift the position of thermodynamic equilibrium in favor of dehydrogenated compounds.

Many different techniques are know for the removal of a substance from a mixture of that substance with others. Examples of such techniques include crystallization, distillation, liquefaction, solvent extraction, absorption, membrane separation and chemical reaction. However, it is in practice difficult to remove hydrogen from a mixture of hydrogen and one or more organic compounds, especially a mixture of hydrogen and dehydrogenatable and dehydrogenated organic compounds.

Numerous processes have been disclosed which involved the removal of hydrogen from a mixture of hydrogen and one or more organic compounds. For example, U.S. Pat. No. 4,788,371 discloses a process for the dehydrogenation of hydrocarbons in which hydrogen obtained by the dehydrogenation of the hydrocarbons is chemically reacted with oxygen gas in the presence of a particular catalyst. The specification refers to several other U.S. Pat. specifications which also disclose processes in which hydrogen is chemically reacted with oxygen gas. A disadvantage of all of these processes is that some of the oxygen gas reacts chemically with organic compounds instead of hydrogen, thus converting them into undesired products.

European Pat. No. A1-0219271 and No. A1-0219272 also disclose processes for the dehydrogenation of hydrocarbons in which hydrogen obtained by the dehydrogenation of the hydrocarbons is removed. In these processes, the dehydrogenation takes place in the presence of a zeolite catalyst, and the hydrogen is removed by chemical reaction with an acidic oxide gas such as sulfur dioxide or nitrous oxide. The processes do not share the disadvantage of the processes which use oxygen gas, because sulfur dioxide and nitrous oxide are not as reactive as oxygen towards the organic compounds. However, the processes appear to be poorly effective for the removal of hydrogen.

It has now been found that hydrogen can be removed very effectively and with high selectivity using certain molecular sieves containing a reducible metal cation.

SUMMARY OF THE INVENTION

The present invention therefore provides a process for the removal of hydrogen from a mixture of hydrogen and one or more organic compounds, which comprises contacting the mixture with a molecular sieve containing a reducible metal cation, said molecular sieve being selectively permeable to hydrogen.

Preferably, the hydrogen has been obtained by the dehydrogenation of dehydrogenatable organic compounds to dehydrogenated compounds. In this case, the one or more organic compounds are the dehydrogenatable and the dehydrogenated compounds.

DESCRIPTION OF THE PREFERRED EMBODIMENTS

It will be appreciated by those skilled in the art that molecular sieves which are selectively permeable to hydrogen in a mixture of hydrogen and one or more organic compounds may easily be identified through their inability to absorb the one or more organic compounds.

The molecular sieves used in the process according to the invention preferably have a pore diameter in the range of about 2.5-15 Å, more preferably in the range of about 2.5-6.0 Å, especially about 2.9-4.2 Å.

Conveniently, the pore diameter of the molecular sieve will be at least 0.3 Å smaller than the molecular diameter of the smallest organic compound, more preferably at least 1 Å, especially at least 1.3 Å.

Molecular sieves are known materials which either occur naturally or are made synthetically. The molecular sieve used in the process according to the invention is conveniently selected from crystalline silicates, metallosilicates, aluminophosphates, silicon aluminophosphates, metallo aluminophosphates, and metallo silicon aluminophasphates. The metallo atom is preferably selected from aluminum, gallium, iron, titanium and boron. For example, the molecular sieve may be selected from crystalline aluminum phosphates and crystalline alumino-, gallo-, and ferro silicates. More preferably, the molecular sieve is a crystalline aluminium silicate, in particular a zeolite. Particularly preferred zeolites are those derived from zeolite A, in particular zeolite 3A and 4A.

The reducible metal cation may be any metal cation capable of being reduced by hydrogen. Preferably it is a cation of a transition metal, a lanthanide or an actinide. For example, the reducible metal cation may be a cation of chromium, cobalt, nickel, tungsten, iron (e.g. $Fe^{2+}$, $Fe^{3+}$) or manganese. $Fe^{3+}$ is especially preferred. It will be appreciated that the molecular sieve may contain more than one reducible metal cation.

According to a preferred aspect of the invention, the molecular sieve containing the reducible metal cation is regenerated by oxidation of the reduced cation, for example by heating in the presence of an oxygen-containing gas such as air. Preferably the molecular sieve containing reduced cation is separated from the organic compounds before the regeneration.

The amount of reducible metal cation contained in the molecular sieve is not critical, but is preferably as large as possible. Conveniently, the molecular sieve contains from about 0.1 to about 25 weight percent of reducible metal cation, preferably from about 0.5 to about 15 weight percent, more preferably from about 1 to about 10 weight percent based upon the total weight of the molecular sieve.

It will be appreciated by those skilled in the art that molecular sieves comprise a skeleton of linked atoms, which skeleton defines pores. In the process according to the invention, the reducible metal cation may be contained within the skeleton or within the pores, for example in ion exchange sites within the pores.

The one or more organic compounds may be solid, liquid or gaseous. Preferably they are gaseous.

Examples of organic compounds include hydrocarbons such as alkanes (e.g. methane, ethane, propane and ethylbenzene), alkenes (e.g. ethene, benzene, tetralin, naphthalene), alcohols, aldehydes, ketones, esters and ethers. Particularly preferred organic compounds are alkanes and alkenes having from 1-30 carbon atoms, preferably 1-10 carbon atoms, especially 1-4 carbon atoms.

The process may conveniently be effected at a temperature in the range of from about 20° C. to about 1,000° C., preferably about 300° C. to about 800° C., more preferably abut 450° C. to about 700° C. The pressure may conveniently be in the range of from about 0.1 bar to about 100 bar, preferably about 0.5 bar to about 50 bar, more preferably, about 0.75 bar to about 10 bar. Most preferably, the pressure is atmospheric.

According to another aspect, the invention provides a process for the preparation of dehydrogenated compounds by subjecting dehydrogenatable organic compounds to a dehydrogenation, in which hydrogen which is obtained as a result of the dehydrogenation is removed according to a process as described hereinbefore.

Dehydrogenatable organic compounds are typically those of which the molecules contain at least two hydrogen atoms on neighboring atoms bound together by a single or double bond, where one of the hydrogen carrying atoms in carbon and the other one is selected from carbon and a multivalent hereto atom such as oxygen, sulfur, nitrogen and boron. However, molecules containing at least one hydrogen atom may be dehydrogenated too, by removing one hydrogen atom from a single (carbon) atom and coupling two radicals thus formed, as exemplified by the dehydrogenative coupling of methane to ethane.

The process of the invention in in principle applicable as a step in any dehydrogenation reaction, and presents advantages whenever the equilibrium between the forward and the reverse reactions does not substantially lie at the dehydrogenation side. Although reactions in the liquid phase are not excluded, preference is given to gas phase reactions. Examples are the preparation of aldehydes or ketones from alcohols (often catalyzed by metallic copper), the preparation of alkenes, alkadienes and alkynes from alkanes (for example the dehydrogenation of propane to propene, or ethyl benzene to sytrene, often catalyzed by chromium oxide on alumina or an iron/potassium catalyst), the preparation of alkenes, alkadienes and alkynes from alkanes (for example the dehydrogenation of propane to propene, or ethyl benzene to sytrene, often catalyzed by chromium oxide on alumina or an iron/potassium catalyst), the preparation of alkanes by the dehydrogenative coupling of lower alkanes (for example, the dehydrogenative coupling of methane to give ethane and higher alkanes), the preparation of aromatics from hydroaromatics (e.g. the Pd-catalyzed reaction of tetralin to naphthalene), and the preparation of alkadienes from alkenes (such as the dehydrogenation and rearrangement of butenes to butadiene and the dehydrogenation of propene to propadiene and propyne).

The process for the preparation of dehydrogenated compounds may comprise sequential or simultaneous dehydrogenation and hydrogen-removal steps.

The molecular sieve containing the reducible metal cation may be obtained by an process known in the art, such as impregnation, "dry" impregnation, synthesis from aqueous solution, or ion-exchange.

The molecular sieve is preferably obtained by ion-exchange, in particular solid-state or aqueous ion-exchange, using a salt of the reducible metal cation or an aqueous or an aqueous solution thereof. For example, a molecular sieve, containing an $Fe^{3+}$ cation may be obtained from zeolite 3A or 4A by solid state or aqueous ion-exchange, using a chloride or nitrate salt of $Fe^{3+}$ or an aqueous solution thereof.

The invention will now be described by the following preparations and examples which are intended to be illustrative and are not to be construed as limiting the scope of the invention.

PREPARATION 1

10.17 g of zeolite 4A (BDH chemicals, 13.9 % wt Na) were combined with 100 ml of a 0.05 M solution of $Fe(NO_3)_3$ in water. The resultant slurry was heated under reflux with stirring for one hour, then filtered off, washed and dried (12 hours at 120° C.). The dried material was then combined with 100 ml of a 0.05 M solution of $Fe(NO_3)_3$ in water. The resultant slurry was heated under reflux with stirring for one hour, then filtered off, washed and dried (12 hours at 120° C.). Elemental analysis of the product showed that is consisted of 4.9% wt Fe. The product was used in Example 1.

PREPARATION 2

14.7 g of zeolite 4A (BDH chemicals, 13.9% wt Na) and $FeCL_3 6H_2O$ (1.45 g) were intensively mixed. The mixture was then heated in air at 100° C./hour until a final temperature of 500° C. was reached. The mixture was then kept at 500° C. for 2 hour, then cooled and washed until free of chloride ions. The resultant material was then dried at 120° C. for 12 hour. The product consisted of 2% wt Fe. It was used in Example 2.

PREPARATIONS 3 TO 7

Following the method described in Preparation 2, products were prepared from various amounts of zeolite 3A (12.9% wt K) or 4A (13.9% wt na) and $FeCl_3 6H_2O$. The amounts of zeolite and $FeCl_3 6H_2O$, and the amounts of Fe contained in the products are given in Table 1. The products were used in Examples 3 to 7.

TABLE 1

| Prep. | Zeolite | Amount of Zeolite g | Amount of $FeCl_3.6H_2O$ g | Fe % wt |
|---|---|---|---|---|
| 3 | 4A | 14.25 | 3.63 | 5 |
| 4 | 4A | 13.95 | 5.08 | 7 |
| 5 | 3A | 14.7 | 1.45 | 2 |
| 6 | 3A | 14.25 | 3.63 | 5 |
| 7 | 3A | 13.95 | 5.08 | 7 |

EXAMPLE 1

A feed consisting of 10% v $H_2$, 10% v $C_3H_8$ and 80% v He was passed over 5 g of the product of Preparation 1 at a flow rate of 10 Nl/hour at 600° C. Analysis of the product showed that $300 \times 10^{-6}$ mole of $H_2$ had been oxidized/g of solid. No propane oxidation products were detected.

EXAMPLES 2 TO 7

A feed consisting of 10% v $H_2$, 10% v $C_3H_6$ and 80% v He or $N_2$ was passed over 0.2 g of the products of each of Preparations 2 to 7 at a flow rate of 2 Nl/hour at 600° C. The results are given in Table 2. The results show that the products of Preparations 2 to 7 are capable of selectively removing hydrogen from a mixture of hydrogen and propene.

TABLE 2

| | Amounts oxidized $10^{-6}$ mole/g of product | |
|---|---|---|
| Example | $H_2$ | $C_3H_6$ |
| 2 | 108 | 3 |
| 3 | 159 | 22 |
| 4 | 392 | 22 |
| 5 | 190 | 3 |
| 6 | not determined | 10 |
| 7 | not determined | 8 |

COMPARATIVE EXAMPLE A

The method of Example 2 was repeated, but using 0.2 g zeolite 4A instead of 0.2 g of the product of Preparation 2. No oxidation of $H_2$ or $C_3H_6$ was observed.

COMPARATIVE EXAMPLE B

A product consisting of 2% wt $Fe^{3+}$ was prepared by introducing iron during the synthesis of an aluminophosphate $AlPO_4 < 11$. $AlPO_4 < 11$ has a pore diameter of approximately 6 Å. Since propane has a molecular diameter of only 4.3 Å, the product should be permeable to propane.

A feed consisting of 10% v $H_2$, 10% v $C_3H_8$ and 80% v He was passed over 5 g of the product at a flow rate of 10 Nl/hour at 60° C. Examination of the reaction products showed that both $H_2$ and $C_3H_8$ had been oxidized, the molar ratio of oxidation products being only 1.7.

COMPARATIVE EXAMPLE C

A feed consisting of 10% v $H_2$, 10% $C_3H_6$ and 80% v He was passed over 1 g of manganese(III) oxide on alumina (prepared by impregnation) at a flow rate of 10 Nl/hour at either 600° or 700° C. In both cases, $H_2$ and $C_3H_6$ were oxidized at the same rate. Furthermore, side reactions such as oligomerization and cracking were observed.

COMPARATIVE EXAMPLE D

The method Comparative Example C was repeated, but using 10% wt iron(III) oxide on alumina instead of 10% wt manganese(III) oxide on alumina. $H_2$ and $C_3H_6$ were both oxidized. Furthermore, side-reactions, mainly olefin polymerization and coking were observed, leading to a substantial pressure increase in the reactor.

The Comparative Examples demonstrate the importance of using a molecular sieve in the process according to the invention which is selectively permeable to hydrogen, and which contains a reducible metal cation.

What is claimed is:

1. A process for the removal of hydrogen from a mixture of hydrogen and one or more organic compounds, which comprises contacting the mixture with a molecular sieve containing a reducible metal cation, said molecular sieve being selectively permeable to hydrogen.

2. The process of claim 1 wherein the hydrogen has been obtained by the dehydrogenation of dehydrogenation organic compounds to dehydrogenated compounds, the one or more organic compounds being the said dehydrogenatable and dehydrogenated compounds.

3. The process in claim 1 wherein the molecular sieve has a pore diameter in the range of from about 2.5 Å to about 15 Å.

4. The process of claim 1 wherein the molecular sieve is selected from the group consisting of crystalline aluminum phosphates, crystalline aluminosilicates, crystalline gallosilicates and crystalline ferro silicates.

5. The process of claim 4 wherein the molecular sieve is a zeolite.

6. The process of claim 5 wherein the zeolite is derived from zeolite 3A or zeolite 4A.

7. The process of claim 1 wherein the reducible metal cation is selected from a cation of chromium, cobalt, nickel, tungsten, iron or manganese.

8. The process of claim 7 wherein the reducible metal cation is $Fe^{3+}$.

9. The process of claim 5 wherein the molecular sieve is separated from the organic compounds and then regenerated by oxidation., 10. The process of claim 1 wherein the one or more organic compounds are selected from alkanes and alkanes having from 1 to 10 carbon atoms.

* * * * *